United States Patent
Tadayon et al.

(10) Patent No.: US 7,683,182 B2
(45) Date of Patent: Mar. 23, 2010

(54) CRYSTAL FORMS OF 2-(3-FLUORO-4-HYDROXYPHENYL)-7-VINYL-1,3-BENZOXAZOL-5-OL

(75) Inventors: Abdolsamad Tadayon, Kirkland (CA); Silvio Iera, Montreal (CA); Hong Wen, Westfield, NJ (US); Marc S. Tesconi, Monroe, NY (US); Mannching Sherry Ku, Thiells, NY (US)

(73) Assignee: Wyeth LLC, Madison, NJ (US)

( * ) Notice: Subject to any disclaimer, the term of this patent is extended or adjusted under 35 U.S.C. 154(b) by 396 days.

(21) Appl. No.: 11/369,405

(22) Filed: Mar. 6, 2006

(65) Prior Publication Data

US 2006/0205798 A1    Sep. 14, 2006

Related U.S. Application Data

(60) Provisional application No. 60/659,459, filed on Mar. 8, 2005.

(51) Int. Cl.
*C07D 263/58* (2006.01)
(52) U.S. Cl. .................. 548/221; 548/224; 548/235
(58) Field of Classification Search ................. 514/375; 548/224, 235, 221
See application file for complete search history.

(56) References Cited

U.S. PATENT DOCUMENTS

| 6,794,403 B2 * | 9/2004 | Malamas et al. ............ 514/375 |
| 6,960,607 B2 | 11/2005 | Malamas et al. |
| 2006/0121110 A1 | 6/2006 | Provost et al. |

OTHER PUBLICATIONS

Vippagunta et al., Advanced Drug Delivery Reviews 48 (2001), p. 3-26.*
Threlfall, Terence L. "Analysis of organic polymorphs. A review," *The Analyst* (1995) 120:2435-2460.
Yu, Lian et al., "Physical characterization of polymorphic drugs: an integrated characterization strategy," *Pharmaceutical Science and Technology Today* (Jun. 1998) 1(3):118-127.

* cited by examiner

*Primary Examiner*—Kamal A Saeed
*Assistant Examiner*—Yong Chu
(74) *Attorney, Agent, or Firm*—Pepper Hamilton LLP

(57) ABSTRACT

The present invention is directed to monohydrate and anhydrate crystal forms of 2-(3-fluoro-4-hydroxyphenyl)-7-vinyl-1,3-benzoxazol-5-ol, an estrogenic receptor modulator useful in the treatment of, for example, diseases related to abnormal levels of estrogen.

13 Claims, 7 Drawing Sheets

CRYSTAL FORMS OF 2-(3-FLUORO-4-HYDROXYPHENYL)-7-VINYL-1,3-BENZOXAZOL-5-OL

CROSS-REFERENCE TO RELATED APPLICATION

This application claims benefit of priority of U.S. Provisional Application Ser. No. 60/659,459 filed Mar. 8, 2005, the entire disclosure of which is incorporated herein by reference in its entirety.

FIELD OF THE INVENTION

The present invention is directed to crystal forms of 2-(3-fluoro-4-hydroxyphenyl)-7-vinyl-1,3-benzoxazol-5-ol, an estrogenic receptor modulator useful in the treatment of, for example, diseases related to abnormal levels of estrogen.

BACKGROUND OF THE INVENTION

The pleiotropic effects of estrogens in mammalian tissues have been well documented, and it is now appreciated that estrogens affect many organ systems. Estrogens can exert effects on tissues in several ways, and the most well characterized mechanism of action is their interaction with estrogen receptors leading to alterations in gene transcription. Estrogen receptors are ligand-activated transcription factors and belong to the nuclear hormone receptor superfamily. Other members of this family include the progesterone, androgen, glucocorticoid and mineralocorticoid receptors. Upon binding ligand, these receptors dimerize and can activate gene transcription either by directly binding to specific sequences on DNA (known as response elements) or by interacting with other transcription factors (such as AP1), which in turn bind directly to specific DNA sequences. A class of "coregulatory" proteins can also interact with the ligand-bound receptor and further modulate its transcriptional activity. It has also been shown that estrogen receptors can suppress NF.kappa.B-mediated transcription in both a ligand-dependent and independent manner.

Accordingly, compounds which are estrogen receptor modulators are useful in the treatment or inhibition of conditions, disorders, or disease states that are at least partially mediated by an estrogen deficiency or excess, or which may be treated or inhibited through the use of an estrogenic agent. Such compounds can be particularly useful in treating a peri-menopausal, menopausal, or postmenopausal patient in which the levels of endogenous estrogens produced are greatly diminished. For example, estrogenic compounds are also useful in inhibiting or treating hot flushes, vaginal or vulvar atrophy, atrophic vaginitis, vaginal dryness, pruritus, dyspareunia, dysuria, frequent urination, urinary incontinence, and urinary tract infections. Other reproductive tract uses include the treatment or inhibition of dysfunctional uterine bleeding and endometriosis.

Certain substituted benzoxazole compounds have been found to be effective estrogenic receptor modulators. An example benzoxazole is 2-(3-fluoro-4-hydroxyphenyl)-7-vinyl-1,3-benzoxazol-5-ol, shown below in Formula I. The effectiveness of this compound as an estrogenic modulator, as well as its preparation, are reported in U.S. Pat. No. 6,794,403, which is incorporated herein by reference in its entirety.

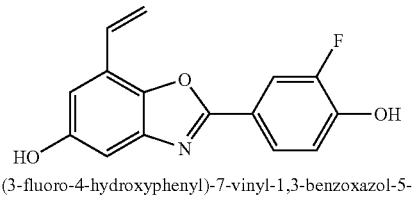

2-(3-fluoro-4-hydroxyphenyl)-7-vinyl-1,3-benzoxazol-5-ol

The crystalline form of a particular drug (e.g., hydrate, solvate, polymorph, etc) is often an important determinant of the drug's ease of preparation, stability, solubility, storage stability, ease of formulation and in vivo pharmacology. Different crystalline forms occur when a compound crystallizes in different lattice arrangements or where solvent molecules (including water molecules) are incorporated into the crystalline lattice, resulting in solids with different thermodynamic properties and stabilities specific to the particular form. It is entirely possible that one crystal form is preferable over another where certain aspects such as ease of preparation, stability, etc. are deemed to be critical. Similarly, greater solubility and/or superior pharmacokinetics may be the desired characteristics.

Because improved drug formulations showing, for example, better bioavailability or better stability are consistently sought, there is an ongoing need for new or purer crystal forms of existing drug molecules. The crystal forms of 2-(3-fluoro-4-hydroxyphenyl)-7-vinyl-1,3-benzoxazol-5-ol described herein are directed toward this end.

SUMMARY OF THE INVENTION

The present invention provides anhydrate and monohydrate crystal forms of 2-(3-fluoro-4-hydroxyphenyl)-7-vinyl-1,3-benzoxazol-5-ol, characterized according to the powder X-ray diffraction data, differential scanning calorimetry, thermogravimetric analysis, and dynamic vapor sorption data provided herein.

The present invention further provides compositions containing the crystal forms of the invention.

The present invention further provides a method of preparing the monohydrate crystal form of the invention comprising precipitating the monohydrate from a solution comprising water.

The present invention further provides a method of preparing the anhydrate crystal form of the invention comprising precipitating the anhydrate from an anhydrous solution.

The present invention further provides compounds prepared by the above methods.

The present invention further provides methods of modulating an estrogen receptor comprising contacting the receptor with a crystal form of the invention.

The present invention further provides methods of treating prostatitis, interstitial cystitis, inflammatory bowel disease, Crohn's disease, ulcerative proctitis, colitis, prostatic hypertrophy, uterine leiomyomas, breast cancer, endometrial cancer, polycystic ovary syndrome, endometrial polyps, endometriosis, benign breast disease, adenomyosis, ovarian cancer, melanoma, prostate cancer, colon cancer, glioma, astioblastomia, free radical induced disease states, vaginal or vulvar atrophy, atrophic vaginitis, vaginal dryness, pruritus, dyspareunia, dysuria, frequent urination, urinary incontinence, urinary tract infections, vasomotor symptoms, arthritis, joint swelling or erosion, joint damage secondary to arthroscopic or surgical procedures, psoriasis, dermatitis, ischemia, reperfusion injury, asthma, pleurisy, multiple sclerosis, systemic lupus erythematosis, uveitis, sepsis, hemmorhagic shock, or type II diabetes, in a mammal in need thereof, which comprises providing to the mammal a therapeutically effective amount of a crystal form of the invention.

The present invention further provides methods of lowering cholesterol, triglycerides, Lp(a), or LDL levels; inhibiting or treating hypercholesteremia, hyperlipidemia, cardiovascular disease, atherosclerosis, hypertension, peripheral vascular disease, restenosis, or vasospasm; or inhibiting vascular wall damage from cellular events leading toward immune mediated vascular damage in a mammal in need thereof, which comprises providing to the mammal a therapeutically effective amount of a crystal form of the invention.

The present invention further provides methods of providing cognition enhancement or neuroprotection; or treating or inhibiting senile dementias, Alzheimer's disease, cognitive decline, stroke, anxiety, or neurodegenerative disorders in a mammal in need thereof, which comprises providing to the mammal an effective amount of the crystal form of the invention.

The present invention further provides methods of inhibiting conception in a mammal in need thereof, which comprises providing to the mammal an effective amount of a crystal form of the invention.

DETAILED DESCRIPTION

Crystalline Forms

Figure 1:
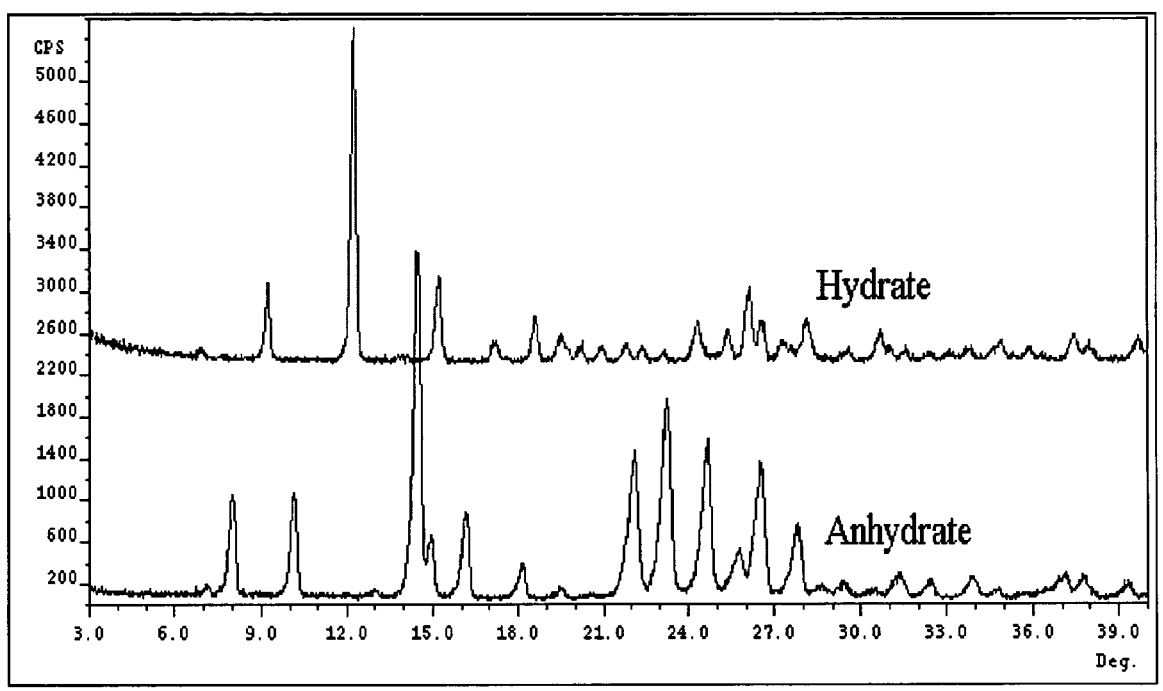
FIG. 1 depicts X-Ray powder diffraction (XRPD) patterns for both the monohydrate (upper) and anhydrate (lower) crystal forms of the invention.

The present invention provides, inter alia, two crystalline forms of 2-(3-fluoro-4-hydroxyphenyl)-7-vinyl-1,3-benzoxazol-5-ol (I), an anhydrate form and a monohydrate form. The crystalline forms of I can be identified by their unique solid state signatures with respect to, for example, differential scanning calorimetry (DSC), X-ray powder diffraction (XRPD), and other solid state methods. Further characterization with respect to water or solvent content of the crystalline forms can be gauged by any of various routine methods such as thermogravimetric analysis (TGA), dynamic vapor sorption (DVS), DSC and other techniques. For DSC, it is known that the temperatures observed will depend upon the rate of temperature change as well as sample preparation technique and the particular instrument employed. Thus, the values reported herein relating to DSC thermograms can vary by plus or minus about 4° C. For XRPD, the relative intensities of the peaks can vary, depending upon the sample preparation technique, the sample mounting procedure and the particular instrument employed. Moreover, instrument variation and other factors can often affect the 2-theta values. Therefore, the peak assignments of diffraction patterns can vary by plus or minus about 0.20. The physical properties and X-ray data distinguishing each of the crystalline forms of the invention are summarized in Tables 1 and 2 below.

TABLE 1

| Monohydrate | | Anhydrate | |
|---|---|---|---|
| Peak position, $2\theta°$ | Peak Description | Peak position, $2\theta°$ | Peak Description |
| 6.9 | W | 7.3 | W |
| 9.2 | S | 8.2 | S |
| 12.2 | Strongest | 10.3 | S |
| 13.9 | W, with a right shoulder | 13.2 | W |
| 15.2 | VS | 14.6 | strongest |
| 17.2 | W | 15.1 | S |
| 17.6 | VW | 16.3 | S |
| 18.6 | M | 18.3 | M |
| 19.5 | M | 19.7 | W |
| 19.7 | M | 20.7 | VW |
| 20.2 | W | 22.3 | S, with a left shoulder |
| 20.9 | M | 23.4 | S |
| 21.8 | M | 24.8 | S |
| 22.4 | W | 25.9 | M |
| 23.1 | W | 26.7 | S |
| 24.3 | S | 28.0 | M |
| 24.6 | VW | 28.8 | W |
| 25.4 | M | 29.5 | W, B |
| 26.2 | M | 30.6 | W, B |
| 26.6 | M | 31.5 | M, B |
| 27.3 | W | 32.6 | W |
| 27.6 | W | 33.0 | VW |
| 28.0 | M | 34.0 | M |
| 29.6 | W | 34.9 | W |
| 30.7 | M | 35.8 | W |
| 31.0 | W | 36.4 | W, sh |
| 31.6 | VW, B | 37.3 | M, B |
| 32.4 | VW, B | 37.9 | M, with a right shoulder |
| 33.1 | W | 39.5 | M |
| 33.8 | M | | |
| 34.6 | M | | |
| 35.9 | M | | |
| 35.3 | W | | |
| 35.8 | W | | |
| 36.3 | VW | | |
| 37.7 | M, B | | |
| 38.0 | M, B | | |
| 39.7 | M, B | | |

VS: very high peak intensity
S: relatively high peak intensity
M: middle range peak intensity
W: relatively weak peak intensity
VW: very weak peak intensity
B: relatively broad peak
sh: shown as a shoulder peak

TABLE 2

| | Monohydrate | Anhydrate |
|---|---|---|
| TGA | 6.1% water (6.23% theory) | less than 0.02% |
| DSC | Dehydration event: onset around ~114° C. (varies) Melt onset ~250° C. | Melt onset ~250° C. |
| XRPD | 9.2, 12.2 °2θ | 8.2, 10.3 °2θ |
| DVS | 0.1% gain (0-90% RH) | 0.2% gain (0-90% RH) |
| Water | 2.34 (pH 7.11) | 10.0 (pH 7.29) |
| Solubility (μg/mL) | 2.21 (pH 7.51) | 12.75 (pH 7.70) |

Figure 2:
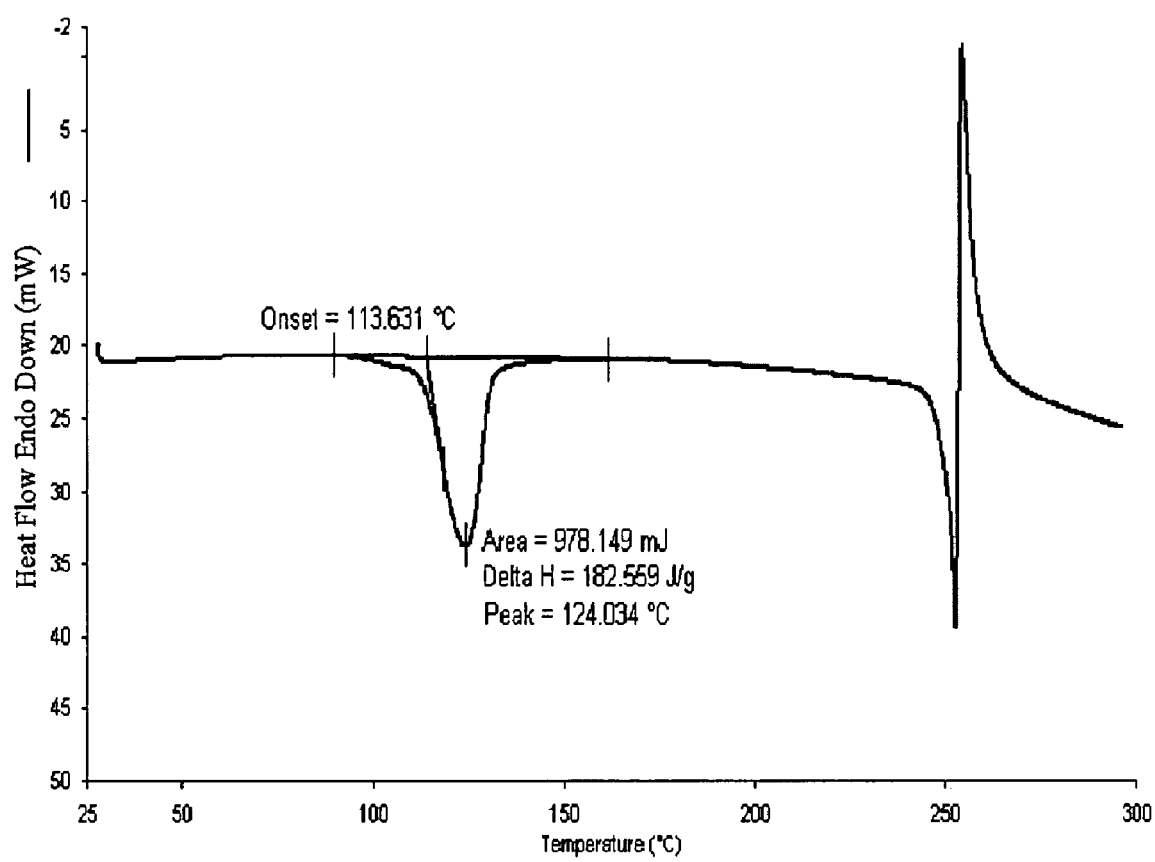
FIG. 2 depicts a differential scanning calorimetry (DSC) thermogram of the monohydrate crystal form of the invention.
Figure 3:
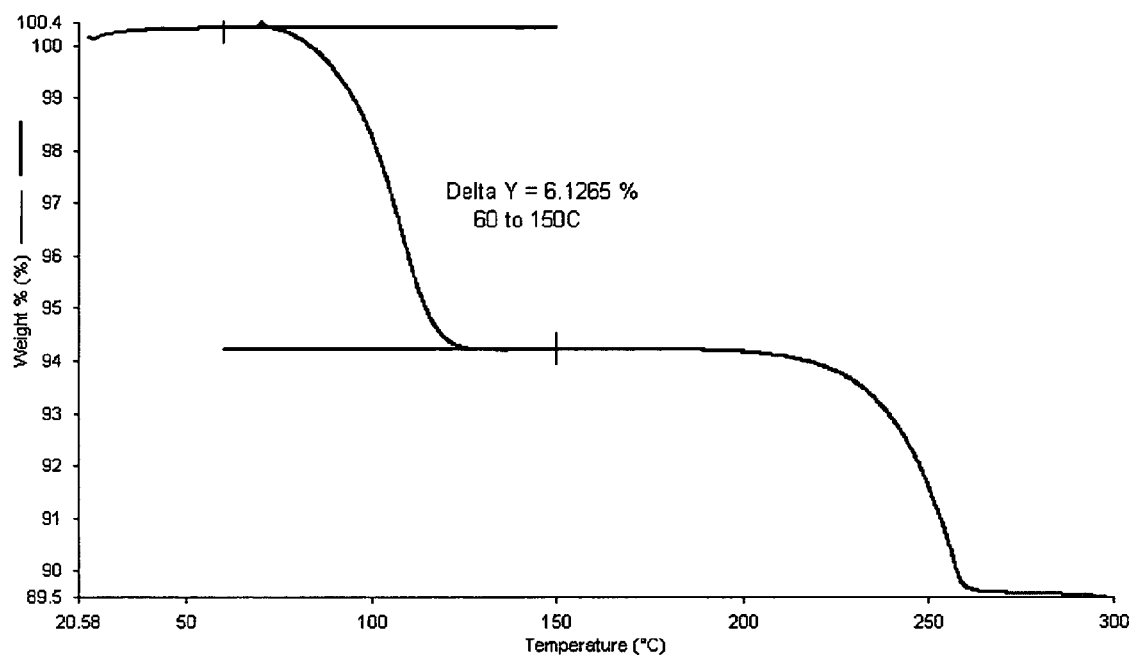
FIG. 3 depicts a thermogravimetric analysis (TGA) of the monohydrate crystal form of the invention.
Figure 5:
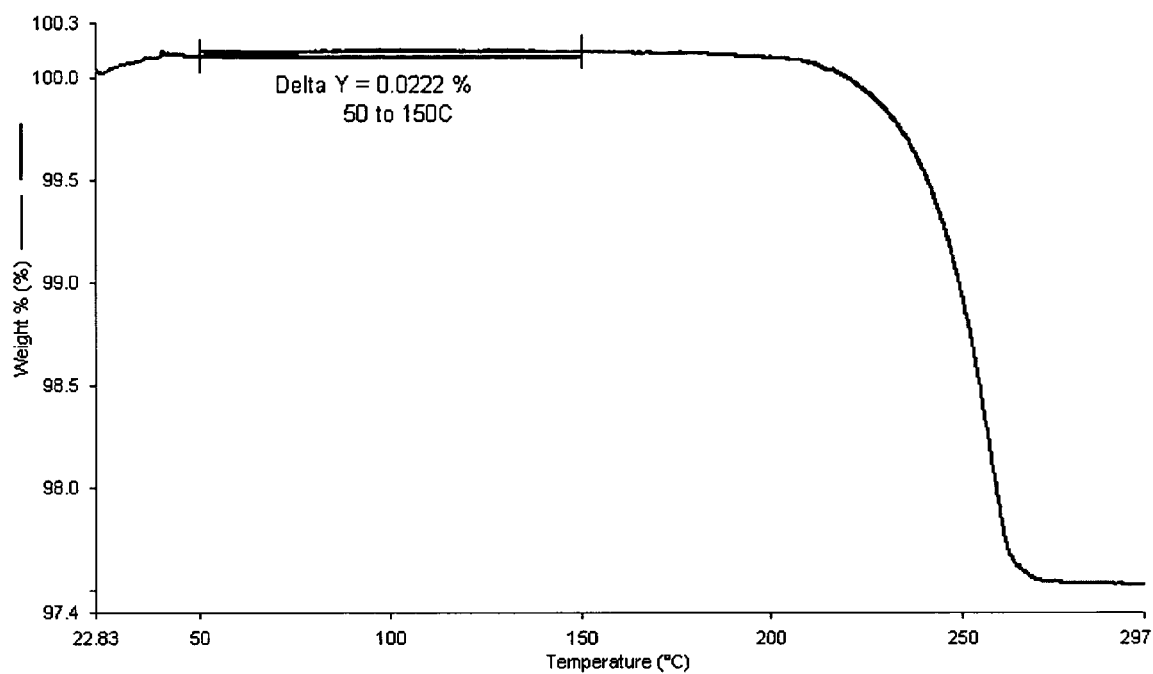
FIG. 5 depicts a thermogravimetric analysis (TGA) of the anhydrate crystal form of the invention.

Data of Table 2 pertaining to water content of the crystalline forms, shows that the monohydrate crystal form was determined to contain close to the theoretical amount of water of 6.23 wt % according to TGA (see, e.g., FIG. 3). DSC confirms the presence of water in the monohydrate, showing a dehydration event around 100° C. (varies from sample to sample, see, e.g., FIG. 2)). In contrast, the anhydrate has essentially no water content, showing less than 0.02% by TGA (FIG. 5) and a lack of a dehydration endotherm in the DSC (FIG. 5).

In accordance with the distinguishing features provided by DSC and TGA analysis, the present invention provides a monohydrate of the compound of Formula I having a differential scanning calorimetry trace comprising a dehydration endotherm. In some embodiments, the monohydrate has a differential scanning calorimetry trace comprising a dehydration endotherm having an onset at about 95 to about 120, about 98 to about 118, or about 95 to about 115° C. In some embodiments, the monohydrate is characterized with a DSC further comprising both a dehydration endotherm and a melting endotherm with an onset of about 250° C. In further embodiments, the monohydrate has a differential scanning calorimetry trace substantially as shown in FIG. 2. In some embodiments, the monohydrate has a thermogravimetric analysis profile showing about 5.0 to about 7.0%, about 5.5 to about 6.5, or about 5.9 to about 6.4% weight loss from about 60 to about 150° C. In further embodiments, the monohydrate has a thermogravimetric analysis profile substantially as shown in FIG. 3.

Figure 4:
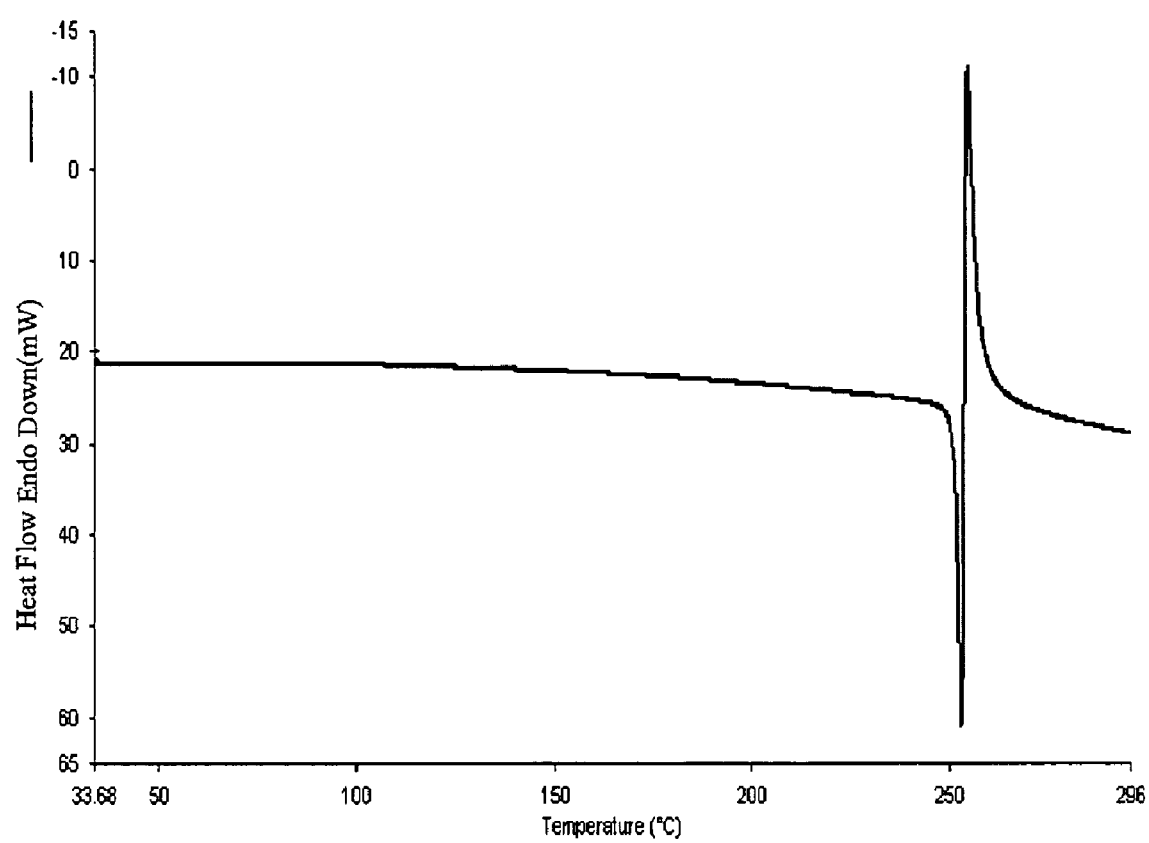
FIG. 4 depicts a differential scanning calorimetry (DSC) thermogram of the anhydrate crystal form of the invention.

The present invention further provides an anhydrous crystal form of the compound of Formula I having a differential scanning calorimetry trace comprising a melting endotherm having an onset at about 250° C. and substantially lacking an endotherm corresponding to a dehydration event. In some embodiments, the crystal form has a differential scanning calorimetry trace substantially as shown in FIG. 4. In further embodiments, the crystal form can have a thermogravimetric analysis profile showing less than about 1%, less than about 0.5%, less than about 0.2%, less than about 0.1%, or less than about 0.05% weight loss from about 60 to about 150° C. In yet further embodiments, the crystal form can have a have a thermogravimetric analysis profile substantially as shown in FIG. 5.

DVS data (see FIGS. 6 and 7) of Table 2 reveal little weight gain for both crystalline forms, indicating that both the monohydrate and anhydrate forms are largely non-hygroscopic. In contrast, water solubility of the two forms shown in Table 2 markedly differ, with the monohydrate having significantly lower solubility than the anhydrate.

The two crystalline forms (see, e.g., FIG. 1) have distinct XRPD patterns, allowing characterization of each the forms based on unique spectral signature.

Accordingly, the present invention provides a monohydrate of the compound of Formula I. In some embodiments, the monohydrate has an X-ray powder diffraction pattern comprising peaks, in terms of 2θ, at about 9.2° and about 12.2°. In some embodiments, the monohydrate has an X-ray powder diffraction pattern comprising peaks, in terms of 2θ, at about 9.2°, about 12.2°, and about 15.2°. In further embodiments, the monohydrate has an X-ray powder diffraction pattern comprising peaks, in terms of 2θ, at about 9.2°, about 12.2°, about 15.2°, and about 24.3°. In yet further embodiments, the monohydrate has an X-ray powder diffraction pattern comprising peaks, in terms of 2θ, about 9.2°, about 12.2°, about 15.2°, about 24.3°, about 25.4° and about 28.0°. In yet further embodiments, the monohydrate has an X-ray powder diffraction pattern substantially as shown in FIG. 1 (upper).

The present invention further provides an anhydrous crystal form of the compounds of Formula I having an X-ray powder diffraction pattern comprising peaks, in terms of 2θ, at about 8.2°, about 10.3°, and about 14.6°. In some embodiments, the crystal form has an X-ray powder diffraction pattern comprising peaks, in terms of 2θ, at about 8.2°, about 10.3°, about 14.6°, about 15.1°, and about 16.3°. In some embodiments, the crystal form has an X-ray powder diffraction pattern comprising peaks, in terms of 2θ, at about 8.2°, about 10.3°, about 14.6°, about 15.1°, about 16.3°, about 22.3°, about 24.8°, and about 26.7°. In further embodiments, the crystal form has an X-ray powder diffraction pattern substantially as shown in FIG. 1 (lower).

Compositions

The present invention further provides compositions containing one or more of the two crystal forms of the invention. In some embodiments, the compositions of the invention include at least about 50%, at least about 60%, at least about 70%, at least about 80%, at least about 90%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, by weight of either the monohydrate or anhydrate crystal form of the compound of Formula I. In some embodiments, the compositions of the invention contain a mixture of the monohydrate and anhydrate crystal forms. In some embodiments, compositions of the invention include the monohydrate or the anhydrate and a pharmaceutically acceptable carrier. In some embodiments, the compositions further include and additional active ingredient such as a progestin.

Preparations

The monohydrate of the invention can be prepared by any of various suitable means. In some embodiments, the process for preparing the monohydrate of the invention involves precipitating the monohydrate from a solution containing water. The solution can further contain one or more additional solvents, such as solvents that are miscible with water. In some embodiments, the solution contains an alcohol such as methanol, ethanol, n-propanol or isopropanol. In some embodiments, the alcohol is ethanol. The solution can contain alcohol or water in any suitable content. In some embodiments, the weight ratio of alcohol to water is about 1:1 to about 3:1, about 1.5:1 to about 2.5:1, or about 2:1. The solution can be prepared by mixing a compound of formula I in water and optionally a solvent. The solution can be optionally heated and/or stirred to help dissolve the compound. Precipitation can be achieved by any suitable means including cooling, adding antisolvent to, or changing pH of the solution, or combination thereof. In some embodiments, the solution is cooled from a temperature of about 65 to about 95, about 70 to about 90, or about 75 to about 80° C. down to a temperature of about −20 to about 50, about 0 to about 20, about 0 to about 10, or about 0 to about 5° C. In some embodiments, the solution is cooled from a temperature of about 75 to about 80 down to a temperature of about 0 to about 5° C. In some embodiments, the solution is held at an intermediate temperature for a period of time before reaching the final cooled temperature. In some embodiments, the intermediate temperature is about 40 to about 60, about 45 to about 55, or about 50° C.

In alternative embodiments, the monohydrate can be precipitated from a solution containing water by adjusting pH of the solution. For example, the pH of a solution can be raised, thereby inducing precipitation of the monohydrate. In some embodiments, the pH is raised from about 7 (or lower) to about 9 or higher. pH can be adjusted according to routine methods such as the addition of a base such as hydroxide (e.g., NaOH). The monohydrate can also be precipitated by addition of antisolvent to a solution in which the compound of Formula I is dissolved. Suitable antisolvents include water or other liquids of the sort. Suitable solvents include alcohols such as methanol, ethanol, n-propanol, isopropanol, or mixtures thereof or other water miscible solvents. The monohydrate can also be prepared by slurrying anhydrous compound of Formula I in water or a solvent containing water (e.g., ethanol/water mixture).

The anhydrate can be prepared by precipitation from an anhydrous solution. An anhydrous solution can contain less than about 1%, less than about 0.5%, less than about 0.2%, less than about 0.1%, less than about 0.05%, or less than 0.01% water. Suitable solvents for precipitating the anhydrate crystal form include hydrocarbons such as pentane, hexanes, heptanes, and the like, ethers such as diethyl ether or tetrahydrofuran, aromatics such as benzene or toluene and the like, chlorinated hydrocarbons such as dichloromethane and the like, as well as other organics such as ethyl acetate and the like, and mixture thereof. In some embodiments, the anhydrate is precipitated from a solvent containing ethyl acetate. In some embodiments, the solvent further contains a hydrocarbon such a heptane. In further embodiments, the weight ratio of ethyl acetate to hydrocarbon is about 3:1 to about 1:1, about 1:1 to about 1:1, or about 1.5:1.

Precipitation of the anhydrate can be induced by any of the various well known methods of precipitation. For example, precipitation can be induced by cooling the solution or addition of antisolvent. In some embodiments, the solution is cooled from a temperature of about 60 to about 90, about 70 to about 85, or about 75 to about 80° C. down to a temperature of about −20 to about 30, about 0 to about 10, or about 0 to about 5° C. During the cooling process, the temperature can be optionally held at an intermediate temperature such as about 40 to about 60° C. (e.g., about 45 to about 50° C.) for a period of time. Antisolvent methods can include addition of suitable antisolvents such as hydrocarbons (e.g., pentane, hexanes, heptanes in which the compound of Formula I is poorly soluble) to a solvent in which the compound of Formula I is dissolved. Suitable solvents include those that at least partially dissolve the compound of Formula I such as ethyl acetate, dichloromethane, tetrahydrofuran, and the like.

Methods of Use and Pharmaceutical Formulations

The crystal forms of this invention are estrogen receptor modulators useful in the treatment or inhibition of conditions, disorders, or disease states that are at least partially mediated by an estrogen deficiency or excess, or which can be treated or inhibited through the use of an estrogenic agent. Accordingly, the present invention provides a method of modulating an estrogen receptor comprising contacting the receptor with a crystal form of the invention. The crystal forms of this invention are particularly useful in treating a peri-menopausal, menopausal, or postmenopausal patient in which the levels of endogenous estrogens produced are greatly diminished. Menopause is generally defined as the last natural menstrual period and is characterized by the cessation of ovarian function, leading to the substantial diminution of circulating estrogen in the bloodstream. As used herein, menopause also includes conditions of decreased estrogen production that may be surgically, chemically, or be caused by a disease state which leads to premature diminution or cessation of ovarian function.

The crystal forms of this invention are also useful in inhibiting or treating other effects of estrogen deprivation including, hot flushes, vaginal or vulvar atrophy, atrophic vaginitis, vaginal dryness, pruritus, dyspareunia, dysuria, frequent urination, urinary incontinence, and urinary tract infections. Other reproductive tract uses include the treatment or inhibition of dysfunctional uterine bleeding. The crystal forms are also useful in treating or inhibiting endometriosis.

The crystal forms of this invention are also active in the brain and are therefore useful for inhibiting or treating Alzheimer's disease, cognitive decline, decreased libido, senile dementia, neurodegenerative disorders, depression, anxiety, insomnia, schizophrenia, and infertility. The crystal forms of this invention are also useful in treating or inhibiting benign or malignant abnormal tissue growth including, glomerulosclerosis, prostatic hypertrophy, uterine leiomyomas, breast cancer, scleroderma, fibromatosis, endometrial cancer, polycystic ovary syndrome, endometrial polyps, benign breast disease, adenomyosis, ovarian cancer, melanoma, prostate cancer, cancers of the colon, and CNS cancers, such as glioma or astioblastomia.

The crystal forms of this invention are cardioprotective and are antioxidants, and are useful in lowering cholesterol, triglycerides, Lp(a), and LDL levels; inhibiting or treating hypercholesteremia, hyperlipidemia, cardiovascular disease, atherosclerosis, peripheral vascular disease, restenosis, and vasospasm; and inhibiting vascular wall damage from cellular events leading toward immune mediated vascular damage. The compounds of this invention are also useful in treating disorders associated with inflammation or autoimmune diseases, including inflammatory bowel disease (Crohn's disease, ulcerative colitis, indeterminate colitis), arthritis (rheumatoid arthritis, spondyloarthropathies, osteoarthritis), pleurisy, ischemia/reperfusion injury (e.g. stroke, transplant rejection, myocardial infarction, etc.), asthma, giant cell arteritis, prostatitis, uveitis, psoriasis, multiple sclerosis, systemic lupus erythematosus and sepsis.

The crystal forms of this invention are also useful in treating or inhibiting ocular disorders, including cataracts, uveitis, and macular degeneration, and in treating skin conditions such as aging, alopecia, and acne.

The crystal forms of this invention are also useful in treating or inhibiting metabolic disorders such as type-II diabetes, of lipid metabolism, and of appetite (e.g. anorexia nervosa and bulimia).

Crystal forms in this invention are also useful in treating or inhibiting bleeding disorders such as hereditary hemorrhagic telangiectasia, dysfunctional uterine bleeding, and combating hemorrhagic shock.

The crystal forms of this invention are useful in disease states where amenorrhea is advantageous, such as leukemia, endometrial ablations, chronic renal or hepatic disease or coagulation diseases or disorders.

The crystal forms of this invention can be used as a contraceptive agent, particularly when combined with a progestin.

Methods of treating the diseases and syndromes listed herein are understood to involve administering to an individual in need of such treatment a therapeutically effective amount of a crystal form of the invention, or composition containing the same. As used herein, the term "treating" in reference to a disease is meant to refer to preventing, inhibiting and/or ameliorating the disease.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual that may be predisposed to the disease, condition or disorder but does not yet experience or display the pathology or symptomatology of the disease;

(2) inhibiting the disease; for example, inhibiting a disease, condition or disorder in an individual that is experiencing or displaying the pathology or symptomatology of the disease, condition or disorder (i.e., arresting or slowing further development of the pathology and/or symptomatology); and (3) ameliorating the disease; for example, ameliorating a disease, condition or disorder in an individual that is experiencing or displaying the pathology or symptomatology of the disease, condition or disorder (i.e., reversing the pathology and/or symptomatology).

As used herein, the term "contacting" refers to the bringing together of indicated moieties in an in vitro system or an in vivo system. For example, "contacting" an estrogen receptor with a crystal form of the invention includes the administration of a crystal form of the present invention to an individual or patient, such as a human, having an estrogen receptor, as well as, for example, introducing a crystal form of the invention into a sample containing a cellular or purified preparation containing the estrogen receptor.

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. Effective administration of the crystal forms of this invention may be given at an oral dose of from about 0.1 mg/day to about 1,000 mg/day. Preferably, administration will be from about 10 mg/day to about 600 mg/day, more preferably from about 50 mg/day to about 600 mg/day, in a single dose or in two or more divided doses. The projected daily dosages are expected to vary with route of administration.

Such doses may be administered in any manner useful in directing the active compounds herein to the recipient's bloodstream, including orally, via implants, parentally (including intravenous, intraperitoneal, intraarticularly and subcutaneous injections), rectally, intranasally, topically, ocularly (via eye drops), vaginally, and transdermally.

Oral formulations containing the active crystal forms of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

In some cases it may be desirable to administer the crystal forms directly to the airways in the form of an aerosol.

The crystal forms of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

In order that the invention disclosed herein may be more efficiently understood, examples are provided below. It should be understood that these examples are for illustrative purposes only and are not to be construed as limiting the invention in any manner.

EXAMPLES

Example 1

Preparation of the Anhydrate Crystal Form

Solid 2-(3-fluoro-4-hydroxyphenyl)-7-vinyl-1,3-benzoxazol-5-ol (170 g, 0.627 mol) was dissolved in ethyl acetate (3946 g, 23 volumes) at 75-80° C. The resulting solution was treated with charcoal (17 g) at 75-80° C. The filtrate was then concentrated at atmospheric pressure to 7 volumes and to the slurry was added heptane (793 g, 6 volumes) while maintaining at 75-80° C., then cooled to 45-50° C., held for 0.5 h, then cooled to 0-5° C., and held for 1 h. The solid was filtered off, dried at 55-65° C., 5-10 mm Hg, to afford an 87% recovery and 99.4% purity.

Example 2

Preparation of the Monohydrate Crystal Form

A 3 L multi-neck flask with agitator, condenser, and temperature probe was charged with 274 g of 2-(3-fluoro-4-hydroxyphenyl)-7-vinyl-1,3-benzoxazol-5-ol and 1375 mL of pre-filtered ethanol. The mixture was heated to 75-80° C. to form a solution after 10 min. Water (688 mL) was added to the solution over the course of 0.5 h at 75-80° C. The solution was then cooled to 50° C. over the course of 0.5 h and subsequently held at 50° C. for another 0.5 h (crystals began to appear at around 74° C.). The resulting suspension was then cooled to 0-5° C. over 0.5 h and held at 0-5° C. for 1 h. The solid was collected by filtration and the cake washed with 2×300 mL ethanol:water (2:1 v/v) precooled to 0-5° C. The washed cake was dried at 32-38° C., 20-25 mmHg for 20 h to give 281.8 g (96.11% yield) of final monohydrate product. Water Content (KF)—6.5%; TGA—6.35% water; DSC and XRPD consistent with monohydrate.

Example 3

Conversion of Anhydrate to Monohydrate pH Method

Anhydrous 2-(3-fluoro-4-hydroxyphenyl)-7-vinyl-1,3-benzoxazol-5-ol (71 mg) was added to 2 mL of water and the mixture was pH adjusted to pH 10 with 1 N NaOH at which point the solution became clear. After 2 hours, the solution became light yellow and cloudy. The solution was centrifuged, the supernatant decanted and the precipitate air dried and then vacuum dried. XRPD and TGA of the product was consistent with the monohydrate.

Solvent/Antisolvent Method

Anhydrous 2-(3-fluoro-4-hydroxyphenyl)-7-vinyl-1,3-benzoxazol-5-ol (about 100 mg) was dissolved in 3 mL of ethanol afterwhich 4 mL water was added slowly until the solution became cloudy. The solution was centrifuged, the supernatant decanted, and the precipitate air dried and then vacuum dried. XRPD and TGA of the product was consistent with the monohydrate.

Aqueous Suspension Method

Anhydrous 2-(3-fluoro-4-hydroxyphenyl)-7-vinyl-1,3-benzoxazol-5-ol (84 mg) was suspended in 4.2 mL of water and stirred at room temperature for 40 hours. The solution was centrifuged, the supernatant decanted, and the precipitate air dried and then vacuum dried. XRPD and TGA was consistent with a mixture of anhydrate and monohydrate (2.4% water content by TGA).

Example 4

Stability Studies

Short Term

XRPD studies revealed that the monohydrate was stable at 70° C. for one hour but partially dehydrated at 90° C. after one half hour, and completely dehydrated at 90° C. after one hour.

Medium Term

Samples of monohydrate were stored at room temperature, 56° C., and 70° C. for one week. At room temperature, humidity was maintained at 0% RH. Humidity was not controlled for the higher temperatures.

The samples were analyzed by XRPD and TGA. Those samples stored at room temperature and 56° C. showed no obvious dehydration after one week. The sample at 70° C. showed no obvious hydration after 1 day, but after 4 days, the sample became partially dehydrated. After 7 days, the sample at 70° C. was mostly dehydrated.

Long Term

Non-micronized samples of monohydrate and anhydrate were stored at 40° C./75% RH for three months. The monohydrate was also stored at 40° C. without humidity control. During the three months, the samples were checked after two weeks, one month, two months, and three months. XRPD and TGA revealed that both the monohydrate and anhydrate did not transform after three months, and HPLC revealed that the samples are chemically stable under the test conditions.

In a separate study, XRPD revealed that micronized samples of anhydrate did not transform to the monohydrate after storage at 25° C./60% RH for three months; however, micronized samples did partially transform to the monohydrate after one month at 40° C./75% RH. In contrast, non-micronized samples of anhydrate stored under the same conditions (40° C./75% RH) did not show any obvious transformation.

Example 5

Acquisition of X-Ray Powder Diffraction Data

X-Ray data (e.g., see FIG. 1 and Table 1) was acquired using an X-ray powder diffractometer (Scintag Inc., Cupertino, Calif.) having the following parameters: voltage 45 kV, current 40.0 mA, power 1.80 kW, scan range (2θ) 3 to 40°, scan step size 0.02°, total scan time 22.6 minutes.

Example 6

Acquisition of Differential Scanning Calorimetry Data

Differential scanning calorimetry data (see FIGS. 2 and 3) were collected using a DSC (Perkin Elmer, Norwalk, Conn.) under the following parameters: 20 mL/min purge gas ($N_2$), scan range 25 to 300° C., scan rate 10° C./min.

Example 7

Acquisition of Thermogravimetric Analysis Data

Thermogravimetric analysis data (see FIGS. 4 and 5) was collected using a TGA instrument (Perkin Elmer, Norwalk, Conn.) under the following parameters: 20 mL/min purge gas($N_2$); scan range 25 to 300° C., scan rate 10° C./min.

Example 8

Acquisition of Dynamic Vapor Sorption Data

Figure 6:
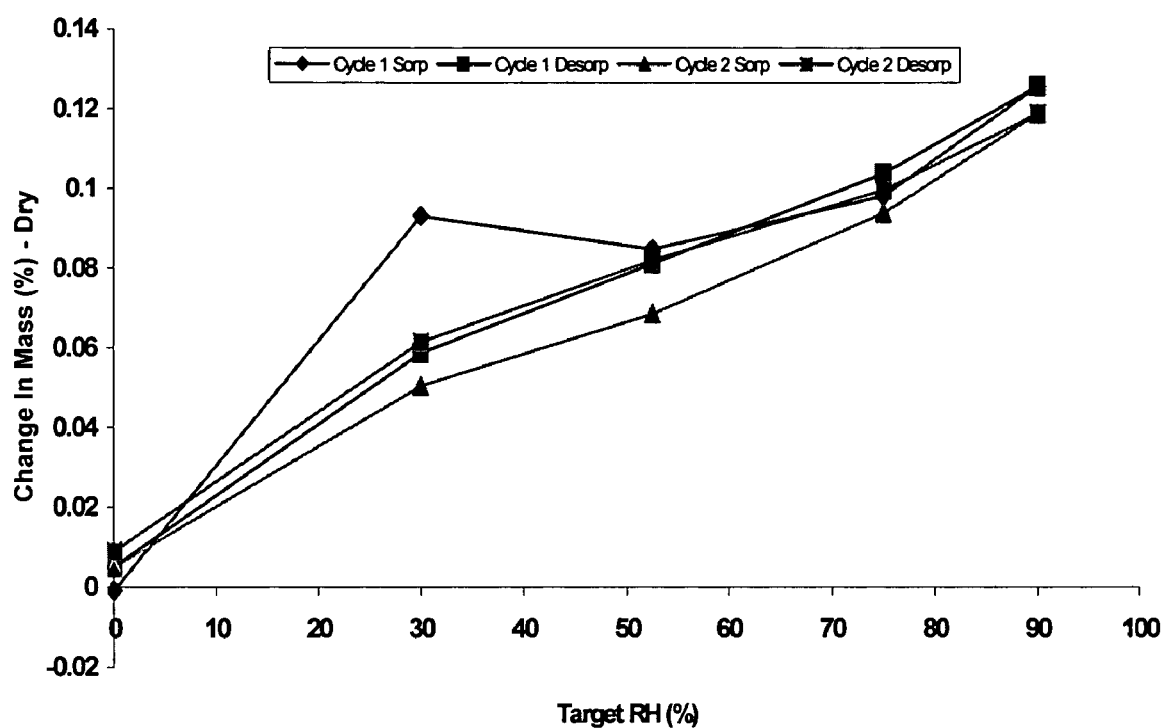
FIG. 6 depicts a dynamic vapor sorption (DVS) isotherm plot for the monohydrate crystal form of the invention.
Figure 7:
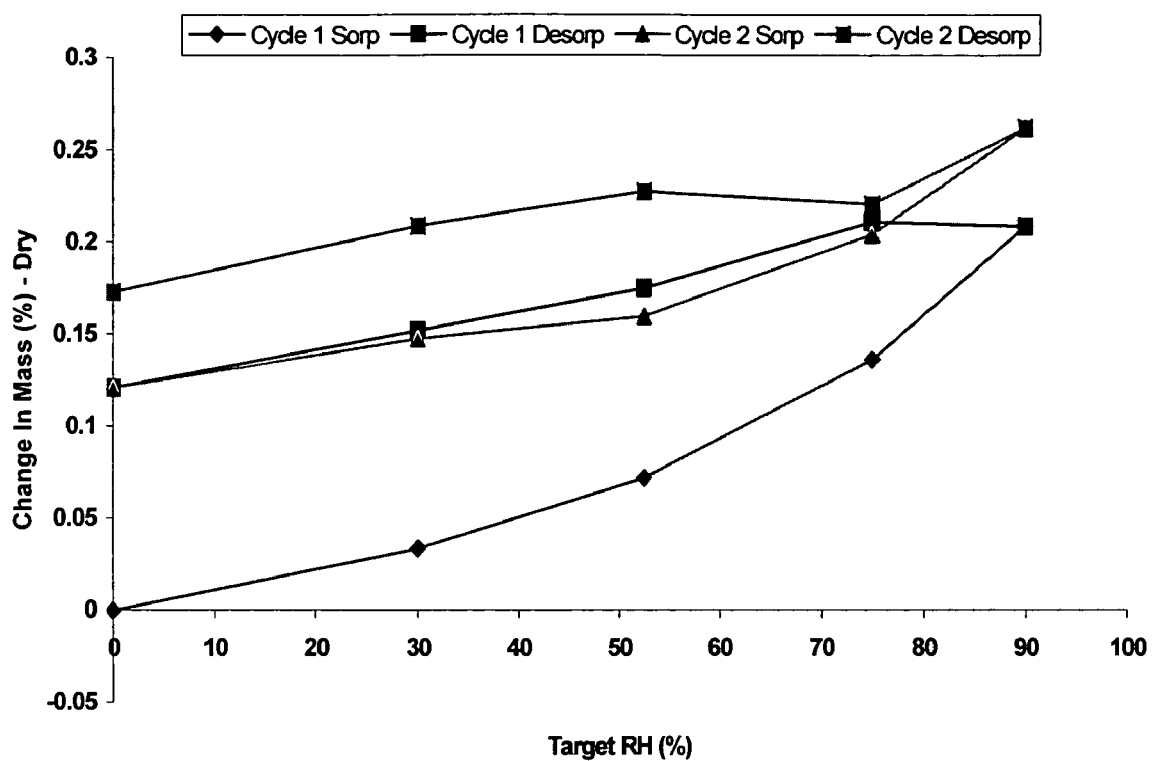
FIG. 7 depicts a dynamic vapor sorption (DVS) isotherm plot for the anhydrate crystal form of the invention.

Dynamic Vapor Sorption (Allentown, Pa.) was used to measure the hygroscopicity of the anhydrate and monohydrate of the invention (see FIGS. 6 and 7). The step conditions were three hours each at 0%, 30%, 52.5%, 75% and 90% RH, two full cycles.

Example 9

Preparation of a Pharmaceutical Formulation and Composition Containing the Anhydrate Crystal Form of the Invention (Unit Dose of 75 mg/Tablet)

The pharmaceutical formulation was prepared by steps 1-7 of the following procedure utilizing the weight/weight percentages (% wt/wt) of the ingredients shown in the table below. The tablets were prepared by steps 8-10 of the following procedure. Each tablet contained the unit dose amounts shown in the table below.

1. An aqueous solution of polyvinylpyrrolidone (povidone K25) and sodium lauryl sulfate in purified water was prepared.

2. The anhydrate crystal form of 2-(3-fluoro-4-hydroxyphenyl)-7-vinyl-1,3-benzoxazol-5-ol was mixed with a portion of mannitol (Pearlitol 200SD), and then the mixture was passed through an appropriate screen and placed in a high shear mixer bowl.

3. The remainder of the mannitol, microcrystalline cellulose (Avicel pH 113), and croscarmellose sodium was passed through an appropriate screen into the mixer bowl and mixed.

4. The blend from Step 3 was granulated using the Step 1 solution, and was followed with additional purified water if needed.

5. The Step 4 granulation was dried and passed through an appropriate screen.

6. The magnesium stearate was passed through an appropriate screen.

7. The magnesium stearate was premixed with an equal portion of the blend in Step 5, and then the premix was added to the remainder of the Step 5 material and mixed in a blender.

8. The final blend from Step 7 was compressed into tablets using a suitable tablet press.

9. A 7.5% solid solution of Opaglos 2 was prepared.

10. A sufficient amount of coating solution was applied on the tablets to provide a 3.0% wt/wt increase in dried tablet weight.

Composition of the Pharmaceutical Formulation and Tablet

| Ingredient | % wt/wt in the pharmaceutical formulation batch | Unit Dose (mg/tablet) |
| --- | --- | --- |
| Anhydrate Crystal Form of 2-(3-fluoro-4-hydroxyphenyl)-7-vinyl-1,3-benzoxazol-5-ol | 25.0 | 75.0 |
| Mannitol (Pearlitol 200SD)[a] | 51.5 | 154.5 |
| Microstalline Cellulose (Avicel PH 113) | 15.0 | 45.0 |
| Croscarmellose Sodium | 4.0 | 12.0 |
| Polyvinylpyrrolidone (Povidone K25) | 2.0 | 6.0 |
| Sodium Lauryl Sulfate | 2.0 | 6.0 |
| Magnesium Stearate | 0.5 | 1.5 |
| Purified Water[b] | — | — |
| Total | 100.0% | 300.0 |
| Film Coat Opaglos 2, green 97W11753 | 3.0 | 9.0 |

[a]If assay is other than 100.0%, adjust the amount of input against mannitol accordingly.
[b]Used in the process, but does not appear in the final tablet product.

Example 10

Preparation of a Pharmaceutical Formulation and Composition Containing the Anhydrate Crystal Form of the Invention (Tablet Unit Dose of 25 mg/Tablet)

The pharmaceutical formulation was prepared by steps 1-7 of the procedure of Example 9, utilizing the weight/weight percentages (% wt/wt) of the ingredients shown in the table below. The tablets were prepared by steps 8-10 of the procedure of Example 9. Each tablet contained the unit dose amounts shown in the table below.

Composition of the Tablet:

| Ingredient | % wt/wt in the pharmaceutical formulation batch | Unit Dose (mg/tablet) |
| --- | --- | --- |
| Anhydrate Crystal Form of 2-(3-fluoro-4-hydroxyphenyl)-7-vinyl-1,3-benzoxazol-5-ol | 25.0 | 25.0 |
| Mannitol (Pearlitol 200SD)[a] | 51.5 | 51.5 |
| Microstalline Cellulose (Avicel PH 113) | 15.0 | 15.0 |
| Croscarmellose Sodium | 4.0 | 4.0 |
| Polyvinylpyrrolidone (Povidone K25) | 2.0 | 2.0 |
| Sodium Lauryl Sulfate | 2.0 | 2.0 |
| Magnesium Stearate | 0.5 | 0.5 |
| Purified Water[b] | — | — |
| Total | 100.0% | 100.0 |
| Film Coat Opaglos 2, green 97W11753 | 3.0 | 3.0 |

[a]If assay is other than 100.0%, adjust the amount of input against mannitol accordingly.
[b]Used in the process, but does not appear in the final tablet product.

Example 11

Preparation of a Pharmaceutical Formulation and Composition Containing the Anhydrate Crystal Form of the Invention (Tablet Unit Dose of 5 mg/Tablet)

The pharmaceutical formulation was prepared by steps 1-7 of the procedure of Example 9, utilizing the weight/weight percentages (% wt/wt) of the ingredients shown in the table below. The tablets were prepared by steps 8-10 of the procedure of Example 9. Each tablet contained the unit dose amounts shown in the table below.

Composition of the Tablet:

| Ingredient | % wt/wt in the pharmaceutical formulation batch | Unit Dose (mg/tablet) |
|---|---|---|
| Anhydrate Crystal Form of 2-(3-fluoro-4-hydroxyphenyl)-7-vinyl-1,3-benzoxazol-5-ol | 5.0 | 5.0 |
| Mannitol (Pearlitol 200SD)[a] | 71.5 | 71.5 |
| Microystalline Cellulose (Avicel PH 113) | 15.0 | 15.0 |
| Croscarmellose Sodium | 4.0 | 4.0 |
| Polyvinylpyrrolidone (Povidone K25) | 2.0 | 2.0 |
| Sodium Lauryl Sulfate | 2.0 | 2.0 |
| Magnesium Stearate | 0.5 | 0.5 |
| Purified Water[b] | — | — |
| Total | 100.0% | 300.0 |
| Film Coat Opaglos 2, green 97W11753 | 3.0 | 3.0 |

[a]If assay is other than 100.0%, adjust the amount of input against mannitol accordingly.
[b]Used in the process, but does not appear in the final tablet product.

Example 12

Preparation of a Pharmaceutical Formulation and Composition Containing the Anhydrate Crystal Form of the Invention (Tablet Unit Dose of 150 mg/Tablet)

The pharmaceutical formulation was prepared by steps 1-7 of the procedure of Example 9, utilizing the weight/weight percentages (% wt/wt) of the ingredients shown in the table below. The tablets were prepared by steps 8-10 of the procedure of Example 9. Each tablet contained the unit dose amounts shown in the table below.

Composition of the Tablet:

| Ingredient | % wt/wt in the pharmaceutical formulation batch | Unit Dose (mg/tablet) |
|---|---|---|
| Anhydrate Crystal Form of 2-(3-fluoro-4-hydroxyphenyl)-7-vinyl-1,3-benzoxazol-5-ol | 25.0 | 150.0 |
| Mannitol (Pearlitol 200SD)[a] | 51.5 | 309.0 |
| Microystalline Cellulose (Avicel PH 113) | 15.0 | 90.0 |
| Croscarmellose Sodium | 4.0 | 24.0 |
| Polyvinylpyrrolidone (Povidone K25) | 2.0 | 12.0 |
| Sodium Lauryl Sulfate | 2.0 | 12.0 |
| Magnesium Stearate | 0.5 | 3.0 |
| Purified Water[b] | — | — |
| Total | 100.0% | 600.0 |
| Film Coat Opaglos 2, green 97W11753 | 3.0 | 18.0 |

[a]If assay is other than 100.0%, adjust the amount of input against mannitol accordingly.
[b]Used in the process, but does not appear in the final tablet product.

Example 13

Preparation of a Pharmaceutical Formulation and Composition Containing the Anhydrate Crystal Form of the Invention (Unit Dose of 75 Mg/Tablet)

The pharmaceutical formulation and tablet were prepared as described for Example 9 except that Opadry AMB, yellow, was substituted for Opaglos 2, green.

Example 14

Preparation of a Pharmaceutical Formulation and Composition Containing the Anhydrate Crystal Form of the Invention (Unit Dose of 25 mg/Tablet)

The pharmaceutical formulation and tablet were prepared as described for Example except that Opadry AMB, yellow, was substituted for Opaglos 2, green.

Example 15

Preparation of a Pharmaceutical Formulation and Composition Containing the Anhydrate Crystal Form of the Invention (Unit Dose of 150 mg/Tablet)

The pharmaceutical formulation and tablet were prepared as described for Example 12 except that Opadry AMB, yellow, was substituted for Opaglos 2, green.

Various modifications of the invention, in addition to those described herein, will be apparent to those skilled in the art from the foregoing description. Such modifications are also intended to fall within the scope of the appended claims. Each reference cited in the present application, including patents, published applications, and journal articles, is incorporated herein by reference in its entirety.

What is claimed is:

1. A crystal form of 1,3-benzoxazol-5-ol monohydrate, having an X-ray powder diffraction pattern comprising a peak, in terms of 2θ, at about 12.2°.

2. The monohydrate of claim 1 having an X-ray powder diffraction pattern comprising peaks, in terms of 2θ, at about 9.2° and about 12.2°.

3. The monohydrate of claim 1 having an X-ray powder diffraction pattern comprising peaks, in terms of 2θ, at about 9.2°, about 12.2°, and about 15.2°.

4. The monohydrate of claim 1 having an X-ray powder diffraction pattern comprising peaks, in terms of 2θ, at about 9.2°, about 12.2°, about 15.2°, and about 24.3°.

5. The monohydrate of claim 1 having an X-ray powder diffraction pattern comprising peaks, in terms of 2θ, at about 9.2°, about 12.2°, about 15.2°, about 24.3°, about 25.4° and about 28.0°.

6. The monohydrate of claim 1 having an X-ray powder diffraction pattern substantially as shown in FIG. 1 (upper).

7. The monohydrate of claim 1 having a differential scanning calorimetry trace comprising a dehydration endotherm.

8. The monohydrate of claim 1 having a differential scanning calorimetry trace comprising dehydration endotherm having an onset at about 95° C. to about 120° C.

9. The monohydrate of claim 1 having a differential scanning calorimetry trace comprising a dehydration endotherm having an onset of about 95° C. to about 120° C. and a melting endotherm having an onset at about 250° C.

10. The monohydrate of claim 1 having a differential scanning calorimetry trace substantially as shown in FIG. 2.

11. The monohydrate of claim 1 having a thermogravimetric analysis profile showing about 5% to about 7% weight loss from about 60° C. to about 150° C.

12. The monohydrate of claim 1 having a thermogravimetric analysis profile showing about 5.9% to about 6.4% weight loss from about 60° C. to about 150° C.

13. The monohydrate of claim 1 having a thermogravimetric analysis profile substantially as shown in FIG. 3.

* * * * *